(12) United States Patent
Vandell

(10) Patent No.: US 8,932,647 B1
(45) Date of Patent: Jan. 13, 2015

(54) FUNCTIONAL BEVERAGE COMPOSITION

(71) Applicant: P-HGH, LLC, Jacksonville, FL (US)

(72) Inventor: Carol Vandell, Medford, OR (US)

(73) Assignee: Matthew F. Taylor, Jr., Jacksonville, FL (US)

(*) Notice: Subject to any disclaimer, the term of this patent is extended or adjusted under 35 U.S.C. 154(b) by 0 days.

(21) Appl. No.: 13/964,085

(22) Filed: Aug. 11, 2013

(51) Int. Cl.
| | |
|---|---|
| *A23L 2/38* | (2006.01) |
| *A23L 2/385* | (2006.01) |
| *A23L 2/52* | (2006.01) |
| *A61K 31/14* | (2006.01) |
| *A61K 31/198* | (2006.01) |
| *A61K 33/00* | (2006.01) |
| *A61K 33/22* | (2006.01) |
| *A61K 33/24* | (2006.01) |
| *A61K 33/34* | (2006.01) |

(52) U.S. Cl.
CPC . *A23L 2/52* (2013.01); *A61K 31/14* (2013.01); *A61K 31/198* (2013.01); *A61K 33/00* (2013.01); *A61K 33/22* (2013.01); *A61K 33/24* (2013.01); *A61K 33/34* (2013.01)
USPC .............................. 424/638; 426/23; 426/590

(58) Field of Classification Search
None
See application file for complete search history.

(56) References Cited

U.S. PATENT DOCUMENTS

| | | | | |
|---|---|---|---|---|
| 5,576,351 | A * | 11/1996 | Yoshimura et al. | 514/565 |
| 2004/0067224 | A1* | 4/2004 | Ernest | 424/94.1 |
| 2005/0064013 | A1* | 3/2005 | Liebrech | 424/439 |
| 2006/0088574 | A1* | 4/2006 | Manning et al. | 424/439 |
| 2006/0115556 | A1* | 6/2006 | Foulger et al. | 426/72 |
| 2006/0134300 | A1* | 6/2006 | Newman | 426/590 |
| 2006/0280840 | A1* | 12/2006 | Robertson | 426/72 |
| 2007/0166411 | A1* | 7/2007 | Anthony et al. | 424/750 |
| 2010/0074969 | A1* | 3/2010 | Hughes et al. | 424/655 |
| 2011/0287109 | A1* | 11/2011 | Bagley et al. | 424/638 |
| 2013/0189399 | A1* | 7/2013 | Ragnarsson et al. | 426/73 |

FOREIGN PATENT DOCUMENTS

| WO | WO 2006052231 A1 * | 5/2006 |
|---|---|---|
| WO | WO 2013002802 A1 * | 1/2013 |
| WO | WO 2013164485 A1 * | 11/2013 |

* cited by examiner

*Primary Examiner* — Robert A Wax
*Assistant Examiner* — Olga V Tcherkasskaya
(74) *Attorney, Agent, or Firm* — Jeffrey C. Maynard

(57) ABSTRACT

A functional beverage that can be used by athletes and bodybuilders for restoring human growth hormones using an HGH precursor. The composition includes water, sweeteners, acids, gums, natural colorants, natural flavors, including pantothenic acid, chromium, copper, choline, and boron. The composition also includes selected amino acids such as L-Leucine, L-Isoleucine, L-Valine, and L-Arginine.

10 Claims, No Drawings

FUNCTIONAL BEVERAGE COMPOSITION

BACKGROUND

The present disclosure relates to a functional beverage drink containing a human growth hormone precursor, in particular, the disclosure relates to a drink for consumption on a daily basis by athletes of all skill levels to aid muscle growth.

There are presently a substantial number of electrolyte drinks on the market that are alleged to replenish essential electrolytes and water lost from the body during physical activity. Physical exercise can be distinguished in different categories i.e. those requiring strength, strength and speed, or endurance. In practice, this can be heavy work, muscle activity under severe conditions (e.g. high temperature, high altitude), leisure sports, or athletic performance.

Athletes who participate in sports at any level, amateur or professional, strive to bring their bodies to a physical state that is optimum for the sport or activity of interest. One factor that enables athletes to participate effectively is a high degree of development of the aerobic capacity and/or strength of skeletal muscles. The inherent problem is a built-in failure in stimulus of production and release of human growth hormone (HGH).

Human growth hormone (HGH) is an endocrine hormone produced by the pituitary gland. Upon its release from the pituitary gland, HGH is converted by the liver and other tissues. The natural production of HGH incrementally decreases in the normal human being after approximately 23 years of age. Its production peaks during adolescence and diminishes with age.

The primary purpose of HGH is that of stimulating growth, cell repair, and cell regeneration. Once the growth period is over, its primary function becomes that of cell regeneration and repair, helping to regenerate skin, bones, heart, lungs, liver, and kidneys to their former youthful cell levels. HGH appears to selectively reduce the fat around the abdomen, hips, waist and thighs while at the same time increasing muscle mass.

The desire to attain, in a rapid manner, the maximum degree of skeletal muscle adaptation to exercise has led some athletes to resort to the use of drugs. Such drugs, particularly steroids, are known to "force" muscle growth to degrees greater than can be achieved by exercise and diet alone. The side effects of steroids are dangerous and unacceptable. Indeed, all professional sports leagues, as well as collegiate athletics, have a long list of potentially performance enhancing substances, many of which may be over-the-counter products, the use of any of which is banned. It is therefore important to provide a natural growth stimulus that does not contain any of the banned ingredients.

Muscle requires a large array of nutrients, including amino acids (which are derived from protein) for growth. Such nutrients have been supplied by ingesting foods and supplements that provide the necessary amounts of protein (the source of amino acids), calories, and other nutrients.

Powders that contain appropriate amino acids are available in cans and jars that come with scoopers for measuring dosages into a glass to which water or other beverage is to be added. Some problems with powders are consuming the powder dry is very difficult, and many of the powders taste bad, even when mixed with water. If mixed with juice or milk, the fructose or lactose of the juice/milk raises blood glucose and insulin levels. Such reconstituted powder products are, however, generally unpalatable and do not, in fact, satisfy the body completely by replenishing all the essential constituents which are lost.

One object of the present disclosure, then, is to provide a new method of stimulating production of HGH for natural muscle growth stimulation, in the form of a tasty, convenient ready-to-drink beverage. The provision of an agonist/inhibition blockade to HGH Releasing Factor is the premise of the use of L-Arginine at basal metabolic levels. Until now, these were only available in a barely palatable powder form because of technical and biochemical difficulty in creating a product that is bioavailable. To stimulate HGH production in this manner goes against the teaching of the prior art because it was believed not to be possible to combine the necessary amino acids with any food for the reasons stated above. The delivery system of the present invention therefore combines the preferred amino acid dosages with ready-to-drink beverages that taste good and are convenient, as opposed to the prior art of powders and pills.

The formulation disclosed herein provides a functional beverage composition including, but not limited to, water, fructose, dietary fiber, and flavoring to provide a more palatable drink with a better balance of amino acids, vitamins, minerals, and HGH precursor as important nutrients for muscle growth and optimum performance.

SUMMARY

Disclosed herein is a ready to drink beverage product for direct increase of human growth hormone (HGH) by using an HGH precursor to stimulate natural production.

It is, therefore, an object of the present disclosure to enable beverage compositions for use in growth stimulation that avoid the disadvantages of the prior art.

It is another object of the present disclosure to enable a method for preparing such beverage compositions.

It is yet another object of the present disclosure to enable a beverage composition that stimulates production of HGH that typically diminishes with age.

It is more specifically an object of the disclosure to provide such a beverage composition that is pleasant tasting.

It is still a further object of the present disclosure to enable a beverage composition that does not contain ingredients that have been banned from use by professional athletes.

In accordance with the above and other objects, a functional beverage drink containing a human growth hormone precursor, optimum quantities of minerals, as well as essential amino acids is disclosed. In particular, a drink for consumption on a daily basis by athletes of all skill levels to aid muscle growth is described.

The various features of novelty that characterize the specific formulation will be pointed out with particularity in the claims of this application.

DETAILED DESCRIPTION

The beverage composition summarized above may be better understood by referring to the following description. This description of an embodiment, set out below to enable one to make and use an implementation of the beverage composition, is not intended to limit the enumerated claims, but to serve as a particular example thereof. Those skilled in the art should appreciate that they may readily use the conception and specific embodiments disclosed as a basis for modifying or designing other formulations for carrying out the same purposes of the present beverage composition. Those skilled in the art should also realize that such equivalent assemblies do not depart from the spirit and scope of the beverage composition described herein, in its broadest form.

L-Arginine is known to be a human growth hormone precursor that stimulates the pituitary gland, which controls body growth. Other essential amino acids contained in the beverage composition of the present formulation are Isoleucine, Leucine, and Valine. In a preferred embodiment, the beverage is consumed on a daily basis, preferably at night before sleeping. While the body is at rest, the HGH precursor works to stimulate muscle growth naturally.

The beverage composition of the present disclosure works to assist the body's own ability to secrete HGH naturally in a manner that is safe and effective. While L-Arginine is useful in stimulating muscle growth, when taken alone, on an empty stomach, it has some disadvantages. In particular, the L-Arginine has an extremely unpleasant taste that makes the oral administration of large dosages difficult and sometimes impossible.

In order to overcome this disadvantage, it is possible to administer high dosages of L-Arginine if the formulation has an acid pH, i.e. less than 7.0. The preferred pH is less than 4.0. By controlling the pH in this way, it has been found that the L-Arginine is more readily accepted by the gastrointestinal tract, that there is minimum depletion of normal body chemicals, and that the composition is pleasant to taste. Moreover, the stability of the composition is improved as a result of ensuring that the composition has an acid pH.

The pH is preferably controlled by the presence of an acceptable acid or acid combination with the L-Arginine. Preferably, the acid or acids are added in an amount that results in a pH of less than 4 when the composition is administered orally. Malic acid and/or other suitable acids may be employed.

In a first embodiment, a ready to drink beverage having an HGH precursor is mixed together using water, sweeteners, acids, flavorings, and a blend of vitamins and minerals. The combination of vitamins and minerals includes Pantothenic Acid, Boron, Chromium, Copper, and Choline. Additional ingredients include L-Arginine, L-Isoleucine, L-Leucine, and L-Valine.

According to methods herein, a beverage composition can be made from reverse osmosis water, selected amino acids, and vitamin/minerals, acids, sweeteners, natural flavors/colorants and a gum blend. The ingredients can be mixed together, and then thermally processed.

In a preferred embodiment, a vitamin/mineral premixture may be formulated comprising the following composition:

| | |
|---|---|
| Pantothenic Acid | 2-8 mg |
| Copper | 0.1-0.4 mg |
| Chromium | 0.01-0.05 mg |
| Choline | 15-45 mg |
| Boron | 0.5-2 mg |
| L-Leucine | 30-75 mg |
| L-Isoleucine | 15-45 mg |
| L-Valine | 15-45 mg |

Using such formulation may result in approximately 50% RDI/8 fl. oz. of pantothenic acid, approximately 10% RDI/8 fl. oz. of copper, and approximately 10% RDI/8 fl. oz. of chromium.

As described in further detail below, the beverage composition of the present disclosure may contain Reverse Osmosis Water (or deionized water), L-Arginine, Crystalline Fructose, Maltodextrin (Dietary Fiber), Erythritol, Natural Flavors, Citric Acid, Natural Colors, Gum Blend (Acacia, Xanthan), Malic Acid, Sucralose, L-Leucine, L-Isoleucine, L-Valine, Choline Bitartrate, Calcium Pantothenate, Sodium Borate, Copper Gluconate, and Chromium Chloride.

Each 1000 g. batch may use approximately 35 g. of mixture with approximately 965 g. of water. Preferably, the mixture contains:

| | |
|---|---|
| Erythritol | approximately 5 g. |
| Fructose | approximately 6.5 g. |
| Sucralose | approximately 0.19 g. |
| Vitamin Pre-mix (above) | approximately 0.875 g. |
| L-Arginine | approximately 12.5 g. |
| Citric Acid | approximately 3.8 g. |
| Malic Acid | approximately 0.5 g. |
| Gums (acacia, xanthan) | approximately 0.8 g. |
| Maltodextrin | approximately 5 g. |

The mixture may contain approximately 3-6 grams of coloring and flavoring, as desired. Additionally, the amount of citric acid and malic acid may be adjusted, as necessary. It is contemplated that several flavors may be formulated. For example, for a Lemon-Lime flavored beverage, the flavoring and coloring may include:

| | |
|---|---|
| Flavor | approximately 2.8 g. |
| Color | approximately 0.4 g. |

For a Mixed Berry flavored beverage, the flavoring and coloring may include:

| | |
|---|---|
| Flavor | approximately 5 g. |
| Color | approximately 1 g. |

For a Peach Mango flavored beverage, the flavoring and coloring may include:

| | |
|---|---|
| Flavor | approximately 3.1 g. |
| Color | approximately  1 g. |

For a Fruit Punch flavored beverage, the flavoring and coloring may include:

| | |
|---|---|
| Flavor | approximately  4 g. |
| Color | approximately 1.4 g. |

For a Strawberry Kiwi flavored beverage, the flavoring and coloring may include:

| | |
|---|---|
| Flavor | approximately  3 g. |
| Color | approximately 0.6 g. |

The beverage may be prepared by agitating a quantity of reverse osmosis water with a quantity of premixture of the vitamins and minerals. A sufficient amount of L-Arginine is added and mixed thoroughly until dissolved. Once all ingredients are thoroughly combined, flavoring and natural colors may be added. A sufficient quantity of malic acid and citric acid is added to adjust the pH to less than 4.0. Preferably the pH is approximately 2.9±0.15.

According to best practices, approximately half of the water is agitated with the pre-mix and L-Arginine, until dissolved. The maltodextrin is added and mixed, until dissolved.

As a separate process, the gum is dry blended with an appropriate portion of fructose. Preferably, the fructose is in crystalline form. The dry blend is slowly added to a sufficient quantity of water using shear mixing. The gum mixture is gradually added to the larger batch with good agitation. A sufficient amount of water is added to assure that all gum mixture transfers to the larger batch and is mixed until the gum is fully incorporated.

The remainder of the fructose, the erythritol, and the sucralose is added and thoroughly mixed. The appropriate colorant, as well as the malic acid and citric acid are added, and mixed thoroughly. The remainder of water is added and mixed.

The solution is heated to approximately 180° F. and the appropriate amount of flavoring is added. Heating is continued to approximately 185°-190° F. and held for approximately 30 seconds at approximately 190° F. While still hot, the solution is placed in bottles. The bottle is then capped and inverted for approximately 1 minute. The bottle may be quick cooled by plunging a sealed bottle in an ice bath.

Each 8-fluid ounce serving contains the following approximate nutrients per serving:

| | |
|---|---|
| Calories | 20-30 |
| Protein | 0 g |
| Carbohydrates | 5-6 g |
| Dietary Fiber | 1 g |
| Fat - total | 0 g |
| Pantothenic acid | 50% |
| Copper | 10% |
| Chromium | 10% |

Other components in an 8 fl. oz. serving may include:

| | |
|---|---|
| Choline | 15-45 mg |
| Boron | 0.5-2 mg |
| L-Arginine | 2-5 g |
| L-Leucine | 30-75 mg |
| L-Isoleucine | 15-45 mg |
| L-Valine | 15-45 mg |

The concepts herein have been described with references to a specific preferred embodiment. While specific values, relationships, materials and steps have been set forth for purposes of describing the basic concepts, it will be appreciated by persons skilled in the art that numerous variations and/or modifications may be made to the formulation as shown in the specific embodiments without departing from the spirit or scope of the basic concepts and operating principles disclosed herein, as broadly described. It should be recognized that, in the light of the above teachings, those skilled in the art could modify those specifics without departing from the concepts taught herein. Having now fully set forth the preferred embodiments and certain modifications of the concept underlying the present formulation, various other embodiments as well as certain variations and modifications of the embodiments herein shown and described will obviously occur to those skilled in the art upon becoming familiar with said underlying concept. It is intended to include all such modifications, alternatives and other embodiments insofar as they come within the scope of the appended claims or equivalents thereof. It should be understood, therefore, that the embodiments might be practiced otherwise than as specifically set forth herein. Consequently, the present embodiments are to be considered in all respects as illustrative and not restrictive.

What is claimed is:

1. A method of preparing a liquid beverage product for consumption by humans for restoring human growth hormone, said method comprising:
  preparing a vitamin premixture comprising:
    Pantothenic Acid;
    Copper;
    Chromium;
    Choline;
    Boron;
    Leucine;
    Isoleucine;
    Valine;
  stirring a quantity of reverse osmosis water;
  adding a quantity of a sweetener to the reverse osmosis water and dissolving said sweetener in the water forming a solution;
  adding a quantity of said vitamin premixture to the solution and dissolving said vitamin premixture in the solution;
  adding a quantity of L-Arginine to the solution;
  preparing a dry blend of gum and fructose;
  dissolving said dry blend in a quantity of water using shear mixing, producing a gum mixture;
  adding said gum mixture to said solution; and
  after thoroughly dissolving all ingredients, adding a quantity of acid to the solution to adjust the pH to less than 4.0.

2. The method of claim 1, in which the pH is adjusted to less than 3.0.

3. The method of claim 1, in which said sweetener is selected from the group consisting of:
  Erythritol;
  Fructose; and
  Sucralose.

4. The method of claim 1, in which said vitamin premixture comprises:
  about 2 mg to about 8 mg of pantothenic acid;
  about 0.5 mg to about 2 mg of boron;
  about 0.01 mg to about 0.05 mg of chromium;
  about 0.1 mg to about 0.4 mg of copper;
  about 15 mg to about 45 mg of L-Isoleucine;
  about 30 mg to about 75 mg of L-Leucine;
  about 15 mg to about 45 mg of L-Valine; and
  about 15 mg to about 45 mg of choline.

5. The method of claim 1, further comprising:
  batch processing said solution, wherein, for each batch of approximately 1000 g, said batch comprises approximately 965 g reverse osmosis water and said quantity of L-Arginine comprises about 1000 mg to about 4000 mg of L-Arginine.

6. The method of claim 1, further comprising:
  adding flavoring and coloring to said solution.

7. The method of claim 1, further comprising:
  heat treating said solution; and
  hot filling said solution into bottles.

8. The method of claim 5, further comprising a mixture comprising:
  approximately 5 g of Erythritol;
  approximately 6.5 g of Fructose;
  approximately 0.19 g of Sucralose;
  approximately 0.875 g of said vitamin premixture;
  approximately 3.8 g Citric Acid;
  approximately 0.5 g Malic Acid;
  approximately 0.8 g Gums; and
  approximately 5 g Maltodextrin.

9. The method of claim 1, further comprising:
  heating said solution to approximately 180° F.;
  adding flavoring to said solution while it is hot;
  increasing the temperature to approximately 185°-190° F. and holding said temperature at approximately 190° F. for approximately 30 seconds;

preparing bottles of said solution while hot; and
quick cooling said bottles of solution.

10. The method of claim 1, said isoleucine being in the form of L-Isoleucine;
said leucine being in the form of L-Leucine; and
said valine being in the form of L-Valine.

* * * * *